(12) United States Patent
Hill et al.

(10) Patent No.: US 6,350,902 B2
(45) Date of Patent: Feb. 26, 2002

(54) PROCESS FOR THE SELECTIVE N-FORMYLATION OF N-HYDROXYLAMINES

(75) Inventors: David R. Hill, Gurnee; Chi-Nung Hsiao, Libertyville; Ravi Kurukulasuriya, Gurnee; Steve Wittenberger, Mundelein, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/822,945

(22) Filed: Mar. 30, 2001

Related U.S. Application Data

(60) Provisional application No. 60/193,973, filed on Mar. 31, 2000, and provisional application No. 60/261,640, filed on Jan. 12, 2001.

(51) Int. Cl.$^7$ .............................................. C07C 259/06
(52) U.S. Cl. ...................... 560/312; 560/129; 562/621; 564/218; 564/219; 564/221; 564/224
(58) Field of Search ................................. 560/129, 312; 564/218, 219, 221, 224; 562/621

(56) References Cited

FOREIGN PATENT DOCUMENTS

WO          9906361          2/1999

OTHER PUBLICATIONS

Blackburn, G.M.; "Kinetics of Hydrolysis and Aminolysis of N–Acetyl–O–formylserinamide", Journal of Chemical Society, B, pp. 826–831, 1971.

Zayia, Gregory H.; "First General Method for Direct Formylation of Kineetically–Generated Ketone Enolates", Organic Letters; vol. 1 No. 7, pp. 989–991, 1999.

*Primary Examiner*—Johann Richter
*Assistant Examiner*—Brian J. Davis
(74) *Attorney, Agent, or Firm*—Gregory W. Steele

(57) ABSTRACT

The instant invention provides a process for the selective N-formylation of N-hydroxylamines.

11 Claims, No Drawings

PROCESS FOR THE SELECTIVE N-FORMYLATION OF N-HYDROXYLAMINES

CROSS-REFERENCE TO RELATED APPLICATIONS

This application claims benefit of U.S. Provisional Patent Applications, Ser. No. 60/193,973, filed Mar. 31, 2000 and Ser. No. 60/261,640 filed Jan. 12, 2001.

TECHNICAL FIELD

This invention relates to a process for the selective N-formylation of N-hydroxylamines.

BACKGROUND OF THE INVENTION

While there are several published methods for the N-formylation of N-hydroxylamines, many of these routes have proven to be problematic. Disproportionation of the hydroxylamine to oximes and formylated primary amines is common, as is the formation of O-formylated and N,O-bisformylated by-products. Methods which have proven to minimize by-product formation often require extended reaction times and elevated temperatures, which are impractical for large-scale preparations. Thus, there is a continuing need for an efficient method of selectively formylating the nitrogen of an N-hydroxylamine.

The instant invention discloses a large-scale synthesis of N-hydroxyformamides from N-hydroxylamines and 2,2,2-trifluoroethylformate. While the formylation of enolates with 2,2,2-trifluoroethylformate has been disclosed (Zayia, G. H. *Organic Lett.* 1999, 1, 989–991), the formylation of N-hydroxylamines with this reagent has not previously been described.

SUMMARY OF THE INVENTION

The process of the instant invention provides a selective N-formylation of N-hydroxylamines to provide N-hydroxyformamides which minimizes by-product formation.

In one embodiment of the instant invention is provided a process for the conversion of an N-hydroxylamine to an N-hydroxyformamide comprising reacting the N-hydroxylamine with 2,2,2-trifluoroethylformate in an optionally buffered solvent.

DETAILED DESCRIPTION OF THE INVENTION

The following terms have the meanings specified:

The term "alkyl," as used herein, represents a monovalent group derived from a straight or branched chain saturated hydrocarbon by the removal of a single hydrogen atom.

The term "$C_1$–$C_4$ alkyl group," as used herein, represents a straight or branched chain saturated hydrocarbon radical having from one to four carbon atoms. Alkyl groups of this invention include methyl, ethyl, propyl, tert-butyl, and the like.

The term "aryl," as used herein, represents phenyl, naphthyl, dihydronaphthyl, tetrahydronaphthyl, indanyl, and indenyl. Aryl groups having an unsaturated or partially saturated ring fused to an aromatic ring can be attached through either the saturated or unsaturated part of the group.

The term "arylalkyl," as used herein, represents an aryl group attached to the parent group through an alkyl group.

The term "buffered solvent," as used herein, represents a solvent containing an agent capable in solution of neutralizing acids and bases and thereby maintaining a pH at or near the original pH of a solution during the course of a reaction. Representative buffering agents carbonate salts such as sodium carbonate, potassium carbonate, calcium carbonate, and the like; bicarbonate salts such as sodium bicarbonate, potassium bicarbonate, and the like; phosphate salts such as potassium phosphate, potassium hydrogenphosphate, sodium dihydrogenphosphate, and the like; tertiary amines such as triethylamine, diisopropylethylamine, and the like; optionally substituted pyridines such as 2,6-lutidine, pyridine, collidine, and the like; imidazole; and carboxylate salts such as sodium formate, potassium carbonate, and the like.

The term "cycloalkyl," as used herein, represents a monovalent saturated cyclic hydrocarbon group.

The term "(cycloalkyl)alkyl," as used herein, represents a cycloalkyl group attached to the parent molecular moiety through an alkylene group.

The term "—$C_2$–$C_8$ dialkyl ether," as used herein, represents —$R^1$—O—$R^2$, wherein $R^1$ and $R^2$ are independently a $C_1$–$C_4$ alkyl group, or, $R^1$ and $R^2$, together with the oxygen atom to which they are attached, form a tetrahydrofuranyl or tetrahydropyranyl ring.

The term "electron-withdrawing group," as used herein, represents a group which draws electrons to itself more than a hydrogen atom occupying the same position in the molecule would. Examples of electron-withdrawing groups include alkanoyl, arylsulfonyl, alkylsulfonyl, and the like.

The term "heteroaryl," as used herein, represents a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isoquinoline, isothiazole, isoxazole, oxadiazole, oxazole, 1,2,3-oxadiazole, pyrazine, pyrazole, pyridazine, pyridine, pyrimidine, pyrroline, quinoline, thiazole, 1,3,4-thiadiazole, thiene, triazole, and tetrazole.

The term "heteroarylalkyl," as used herein, represents a heteroaryl group attached to the parent molecular moiety through an alkyl group.

The term "N-hydroxylamine," as used herein, represents $NHR^3(OR^4)$, wherein $R^3$ is any group considered by those skilled in the art to be stable under the reaction conditions; and $R^4$ is selected from the group consisting of hydrogen, alkyl, aryl, arylalkyl, cycloalkyl, (cycloalkyl)alkyl, heteroaryl, and heteroarylalkyl.

The term "N-hydroxyformamide," as used herein, represents $NR^3(CHO)(OR^4)$, wherein $R^3$ and $R^4$ have been previously defined.

The term "substituted pyridine," as used herein, represents a pyridine optionally substituted with one, two, or three methyl groups. Examples of substituted pyridines include 2-picoline; 3-picoline; 4-picoline; 2,6-lutidine; 2,5-lutidine; 2,4-lutidine; 2,4,6-collidine; 2,3,5-collidine; and the like.

Synthetic Processes

The compounds and process of the instant invention will be better understood in connection with the following synthetic scheme which illustrates the method by which the compounds of the instant invention are prepared.

Scheme 1

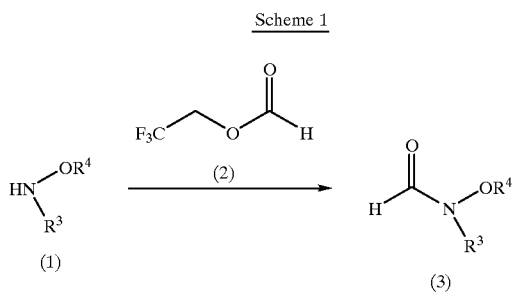

As shown in Scheme 1, compounds of formula (1) can be converted to compounds of formula (3) by treatment with 2,2,2-trifluoroethyl formate (2), which can be prepared according to the procedure described in *J. Chem. Soc.* B 1971, 826–831. Examples of solvents used in these reactions include tetrahydrofuran, methyl tert-butyl ether, diethyl ether, ethyl acetate, isopropyl acetate, 2,2,2-trifluorethanol, formic acid, toluene, and mixtures thereof. The reaction temperature is about 35° C. to about 75° C. and depends on the solvent chosen. Reaction times are typically about 4 to about 18 hours. When the compounds of formula (1) or the compounds of formula (3) are acid-sensitive, the reaction is preferably buffered. Representative buffering agents include carbonate salts, bicarbonate salts, phosphate salts, tertiary amines, optionally substituted pyridines, imidazole, and carboxylate salts. Preferably, the buffer is either imidazole or a carboxylate salt. More preferably, the buffer is either imidazole or sodium formate.

EXAMPLE 1

(1S)-2-(4,4-dimethyl-2,5-dioxo-1-imidazolidinyl)-1-(((4'-(trifluoromethoxy)(1,1'-biphenyl)-4-yl)oxy)methyl)ethyl-(N-hydroxy)formamide A solution of 3-((2S)-2-(N-hydroxyamino)-3-((4'-(trifluoromethoxy)(1,1'-biphenyl)-4-yl)oxy)propyl)-5,5-dimethyl-2,4-imidazolidinedione, para toluene sulfonic acid salt (1.95 kg, prepared according to the procedure described in commonly owned WO 99/06361) in 15% (w/w) potassium carbonate (4.29 kg), tetrahydrofuran (5.07 kg), and methyl tert-butyl ether (4.12 kg) was stirred until all solids dissolved and separated into an aqueous fraction and an organic fraction. The organic fraction was washed with 25% (w/w) sodium chloride (3.83 kg), treated with tetrahydrofuran (0.58 kg), and concentrated to provide a 20–30% (w/w) solution of the free base. The solution was treated with the 2,2,2-trifluoroethyl formate reagent (5.27 kg of the 71.9% (w/w) solution (3.79 kg, 10 equivalents), stirred at reflux for 4 hours, cooled to less than 30° C., treated with water (5.33 kg) and methyl tert-butyl ether (7.62 kg), washed with 15% (w/w) potassium bicarbonate (5.3 kg portions) until the pH of the wash was ≧8, and concentrated. The residue was dissolved in ethyl acetate (7.133 kg), treated with heptane (10.71 kg) during which a solid began to precipitate, stirred for 18 hours, and filtered. The filter cake was rinsed with 1:2 (v/v) ethyl acetate/heptane (5.63 kg), suction dried, then vacuum dried (100 mm Hg) at 100° C. with a nitrogen bleed to provide 2.685 kg (91.8%, ≧99% ee) of the desired product. $^1$H NMR (300 MHz, DMSO-$d_6$) δ 9.95 (br s, 0.5H), 9.80 (br s, 0.5H), 8.41 (br s, 0.5H), 8.37 (br s, 0.5H), 8.35 (s, 0.5H), 7.95 (s, 0.5H), 7.76 (d, 2H, J=8.9 Hz), 7.65 (d, 2H, J=8.5 Hz), 7.43 (d, 2H, J=8.5 Hz), 7.04 (d, 2H, J=8.9 Hz), 4.92–4.80 (m, 0.5H), 4.50–4.38 (m, 0.5H), 4.28–4.06 (m, 2H), 3.82–3.68 (m, 1H), 3.66–3.54 (m, 1H), 3.88 (s, 3H), 3.84 (s, 3H).

EXAMPLE 2

N-hydroxy((1S)-1-phenylethyl)formamide

EXAMPLE 2A (1S)-N-((4-methoxyphenyl)methylidene)-1-phenylethanamine

A mixture of p-anisaldehyde (11.24 g, 82.5 mmol) and (S)-α methyl benzyl amine (10.0 g, 82.5 mmol) in toluene (100 mL) was heated to reflux with removal of water by a Dean-Stark apparatus. After cooling to ambient temperature, the mixture was concentrated to provide 20.15 g (100%) of the desired product. $^1$H NMR (300 MHz, CDCl$_3$) δ 8.30 (s, 1H), 7.75–7.68 (m, 2H), 7.45–7.15 (m, 5H), 4.50 (q, 1H, J=6.6 Hz), 3.82 (s, 3H), 1.58 (d, 3H, J=6.6 Hz).

EXAMPLE 2B

N-((1S)-1-phenylethyl)hydroxylamine

A −78° C. solution of Example 2A (7.15 g, 30 mmole) in tetrahydrofuran (75 mL) was treated with a solution of 3-chloroperoxybenzoic acid (15 g, 60 mmol), warmed to 0° C., stirred for 2 hours, diluted with ethyl acetate (100 mL), washed sequentially with 10% (w/w) sodium thiosulfate, saturated sodium bicarbonate, and brine, dried (MgSO$_4$), filtered, and concentrated. The concentrate was dissolved in tetrahydrofuran (100 mL), treated with p-toluene sulfonic acid monohydrate (8.15 g, 42.8 mmol), stirred for 2 hours, treated with a solution of N-hydroxylamine hydrochloride (8.7 g) in water (15 mL), and stirred for 16 hours. The mixture was diluted with ethyl acetate (100 mL), washed with saturated sodium bicarbonate and brine, dried (MgSO$_4$), filtered, and concentrated. The concentrate was purified by flash column chromatography on silica gel with 1:2 ethyl acetate/hexanes to provide 3.53g (86% yield) of the desired product. $^1$H NMR (300 MHz, CDCl$_3$) δ 7.36–7.20 (m, 5H), 4.09 (q, 1H, J=6.6 Hz), 1.48 (d, 3H, J=6.6 Hz).

EXAMPLE 2C

N-hydroxy((1S)-1-phenylethyl)formamide

A solution of Example 2B (1.5 g, 10.95 mmol) in tetrahydrofuran (15 mL, 10 vols) was treated with the 2,2,2-trifluoroethyl formate reagent (92% wt, 7.6 g, 54.7 mmol, 5 equiv). The resulting mixture was heated at 65° C. for 18 hours and concentrated. The concentrate was distilled under vacuum (170° C. at 1.6 mm Hg) to provide 1.6 g (89%) of the desired product. $^1$H NMR (300 MHz, CDCl$_3$) δ 8.00 (s, 1H), 7.54–7.30 (m, 5H), 4.93 (q, 1H, J=7 Hz), 1.82 (d, 3H, J=7 Hz).

EXAMPLE 3 benzyl-(N-hydroxy)formamide

A suspension of N-benzyl-N-hydroxylamine hydrochloride (1.0 g, 6.26 mmol; Aldrich Chemical Company, Milwaukee, Wis.) in methyl tert-butyl ether (10 mL) was vigorously stirred 10% potassium bicarbonate solution and separated into an aqueous fraction and an organic fraction. The organic fraction was treated with the 2,2,2-trifluoroethyl formate reagent (92% (w/w), 4.35 g, 31.3 mmol, 5 equiv), and heated at reflux for 6 hours. The mixture was washed sequentially with water, 15% potassium bicarbonate, and 15% brine, then concentrated to provide 0.90 g (96%) of the desired product as a mixture of rotamers. $^1$H NMR (300

MHz, CDCl$_3$) δ 8.28, 7.86 (2s, 1H total), 7.35–7.15 (m, 5H total), 7.10, 6.90 (2 br s, 1H total), 4.64, 4.56 (2s, 2H total).

EXAMPLE 4

(1S)-1-((4S)-2,2-dimethyl-1,3-dioxolan-4-yl)-2-((4-(4'-(trifluoromethoxy)phenoxy)phenyl)sulfonyl)ethyl (hydroxy)formamide

EXAMPLE 4A 1-(methylsulfonyl)-4-(4'-(trifluoromethoxy) phenoxy)benzene

A solution of 1-fluoro-4-(methylsulfonyl)benzene (2.2 kg), KOH (906.3 g), 4-(trifluoromethoxy)phenol (2.364 kg) and DMSO (4.4 L) was heated to 90° C. and stirred until HPLC showed <0.5% starting material remained (about 10 hours). HPLC conditions: Zorbax SB-C8 4.6 mm×25 cm; mobile phase was a gradient of 70% water with 0.1% H$_3$PO$_4$/30% acetonitrile to 10% water with 0.1% H$_3$PO$_4$/90% acetonitrile over 15 minutes at a flow rate of 1.5 mL/min, followed by a five minute hold at 10/90; UV detection at 220 nM. Retention times: starting sulfone, 4.5 min; desired product, 7.8 min.

The reaction mixture was cooled to room temperature, diluted with water (8.8 kg), and extracted with two portions of toluene (24 L and 4.7 L). The combined extracts were washed with 1N NaOH solution (11 kg) and water (2×11 kg), filtered, concentrated to a volume of approximately 6 L, treated with heptane (22 L) with agitation, stirred for 2 hours, and cooled to 0–5° C. until the mother liquor was assayed for the desired product at <5 mg/mL. The precipitate was filtered, washed with heptane (6.6 L) and dried under vacuum (100 mm Hg with nitrogen sweep) at 40° C. to provide 2.0 kg (96.4% wt potency, 89.6% yield) of the desired product. Recrystallization from methanol/water (4:8 v/v) gave the purified product with 98% recovery.

$^1$H NMR (300 MHz, CDCl$_3$) δ 7.9 (d, 2H), 7.3 (br d, 2H), 7.1 (d, 4H), 3.1 (s, 3H).

EXAMPLE 4B 1-((4R)-2,2-dimethyl-1,3-dioxolan-4-yl)-2-((4-(4'-(trifluoromethoxy)phenoxy)phenyl)sulfonyl) ethanone A solution of Example 4A (3.327 kg, 98.7% potency, 9.88 mol) in THF (23 L, pre-dried with 3Å molecular sieves) in a flask equipped with an overhead stirrer, an addition funnel, a temperature probe, and a nitrogen inlet was cooled to <−40° C. and treated with 1M LiHMDS in THF (10.08 L, 10.08 mmol) at such a rate as to keep the internal temperature <−40° C. The solution was treated with 2.28M n-butyllithium in hexanes (2.275 L, 5.187 mol), treated with 2.42M n-butyllithium (2.143 L, 5.187 mol) at such a rate as to keep the internal temperature <−40° C., and stirred for 2 hours. The solution was treated with a solution of (R)-methyl-O-isopropylidene glycerate (1.77 kg, 11.066 mol, 1.12 equivalents) in THF (1.77 kg) at such a rate as to keep the internal temperature <−40° C. The resulting mixture was stirred until <1% starting material was observed by HPLC (about 1 hour). HPLC conditions: Zorbax SB-C8 4.6 mm×25 cm column; mobile phase was a gradient of 70% water with 0.1% H$_3$PO$_4$/30% acetonitrile to 10% water with 0.1% H$_3$PO$_4$/90% acetonitrile over 15 minutes at a flow rate of 1.5 mL/min; followed by 5 minute hold at 10/90; UV detection at 210 nM. Retention times: starting material, 7.8 min; desired product, 15.2 min.

The mixture was warmed to −25° C. and the reaction was adjusted to pH 5.5 with 2N H$_2$SO$_4$ (a pH range between 4–6 was optimal to avoid cleavage of the acetonide group and racemization). The internal temperature of the reaction mixture was allowed to rise to between 0° C. and 5° C. during the acid addition giving a clear biphasic solution and allowing accurate measurement of the pH via a pH meter. The solution was treated with isopropyl acetate (33.27 L), stirred, and allowed to settle. The organic phase was washed sequentially with water (14.48 L), 5% NaHCO$_3$ solution (14.65 kg), and 15% NaCl solution (14.50 kg), and azeotropically distilled with THF until <10% isopropyl acetate remained as determined by gas chromatography. GC-FID conditions: Stabilwax-DB column (Restek Corp. cat#10823, lot#15531A, L=30 m, ID=0.25 mm), heater at 250° C., oven temperature gradient: 40° C. for 0 to 4 min then 10° C./min to 100° C., then hold at 100° C. 10 min, post-run 5 min; 1 μL injection volume. Peak identification: THF, 4.12 min; isopropyl acetate, 4.34 min.

The solution was filtered and concentrated to a weight of approximately 8 kg to provide a solution of the desired product which was used without further purification. However, the final product could be purified by crystallization from isopropyl acetate to provide a white crystalline solid.

$^1$H NMR (300 MHz, CDCl$_3$) δ 7.93–7.85 (m, 2H), 7.33–7.25 (m, 2H), 7.20–7.05 (m, 4H), 4.62 (d, 1H), 4.58–4.52 (dd, 1H), 4.30 (d, 1H), 4.22–4.09 (m, 2H), 1.46 (s, 3H).

EXAMPLE 4C 1-((4R)-2,2-dimethyl-1,3-dioxolan-4-yl)-2-((4-(4'-(trifluoromethoxy)phenoxy)phenyl)sulfonyl)ethanol A mixture of NaBH$_4$ (240 g) and ethanol (9.8 L) at −5° C. was treated with Example 4B (either isolated or as a THF solution) (4.53 kg, 10.53 mol by assay) and stirred until HPLC showed none of the starting ketone remaining. HPLC conditions: Zorbax SB-C8 4.6 mm×25 cm, mobile phase was a gradient of 70% water with 0.1% H$_3$PO$_4$/30% acetonitrile to 10% water with 0.1% H$_3$PO$_4$/90% acetonitrile over 15 minutes at a flow rate of 1.5 mL/min; followed by 5 minute hold at 10/90; UV detection at 220 nM. Retention times: starting material, 15 min; desired products (2 diastereomers), 7.8 and 7.9 min.

The mixture was quenched with 2N acetic acid at such a rate as to keep the internal temperature <30° C., concentrated under vacuum at <40° C. to a volume of approximately 9.8 L, and dissolved in ethyl acetate (49 L). The mixture was washed with water (24.5 L) and 15% wt NaCl solution (24.5 L), concentrated to a volume of approximately 9.8 L, azeotropically distilled with ethyl acetate (49 L) to a final volume of approximately 9.8 L, and dissolved in ethyl acetate (44 L) to provide a solution of the desired product which was used directly in the next step.

$^1$H NMR (300 MHz, CDCl$_3$) δ 7.9 (d, 2H), 7.3 (br d, 2H), 7.1 (m, 4H), 4.1–3.9 (m, 4H), 3.55 (dd, 1H), 3.4–3.1 (m, 3H), 1.43, 1.35, 1.30, 1.23 (s, s, s, s, total of 6H from 2 diastereomers).

EXAMPLE 4D (4S)-2,2-dimethyl-4-((E)-2-((4-(4'-(trifluoromethoxy)phenoxy)phenyl)sulfonyl) ethenyl)-1,3-dioxolane A solution of Example 4C in ethyl acetate (5.00 kg, 10.53 mol theoretical) and triethylamine (4.32 kg) was cooled to −5° C., treated with methanesulfonyl chloride (1.94 kg) at such a rate as to maintain the internal reaction temperature at <10° C., stirred at 0–5° C. for 1 hour, and then warmed to room temperature until HPLC showed no more than 0.5% starting material or mesylate intermediate (about 4–8 hours). HPLC conditions: Zorbax SB-C8 4.6 mm×25 cm, mobile phase was a gradient of 70% water with 0.1% $H_3PO_4$/30% acetonitrile to 10% water with 0.1% $H_3PO_4$/90% acetonitrile over 15 minutes at a flow rate of 1.5 mL/min; followed by 5 minute hold at 10/90; UV detection at 220 nM. Retention times: starting material, 7.8 and 7.9 min; mesylate intermediate, 15.5 min; product, trans vinyl sulfone, 16.0 min; cis vinyl sulfone, 17.1 min. Typical trans/cis ratio is 10:1.

The reaction was quenched with water (14.6 kg) and the organic layer was washed with 10% wt citric acid solution (19.6 kg), followed successively by 10% wt $NaHCO_3$ solution (19.6 kg) and water (19.6 kg). The organic layer was concentrated to a volume of approximately 9.8 L, azeotropically distilled with MTBE (2×49L), and concentrated to a final volume of approximately 9.8 L. The residue was dissolved in MTBE (49 L), and assayed for residual ethyl acetate by gas chromatography. If ethyl acetate was <5% in area, additional MTBE (25 L) was added to provide the desired product as a solution. If ethyl acetate was >5% in area, an additional azeotropic distillation with MTBE was performed.

$^1$H NMR (300 MHz, $CDCl_3$) δ 7.1 (m, 4H), 6.9 (dd, 1H), 6.65 (dd, 1H), 4.7 (m, 1H), 4.2 (dd, 1H), 3.7 (dd, 1H), 1.43 (s, 3H), 1.4 (s, 3H).

EXAMPLE 4E (4S)-4-((1S)-1-(hydroxyamino)-2-((4-(4'-(trifluoromethoxy)phenoxy)phenyl)sulfonyl)ethyl)-2,2-dimethyl-1,3-dioxolane A solution of Example 4D in MTBE was cooled to −15° C., treated with 50% wt aqueous $NH_2OH$ over a period of 30 minutes at such a rate as to keep the internal temperature between −10° C. and −15° C., and stirred until HPLC showed <0.5% starting material (about 7 to 20 hours). HPLC conditions: Zorbax SB-C8 4.6 mm×25 cm, mobile phase was a gradient of 70% water with 0.1% $H_3PO_4$/30% acetonitrile to 10% water with 0.1% $H_3PO_4$/90% acetonitrile over 15 minutes at a flow rate of 1.5 mL/min; followed by 5 minute hold at 10/90; UV detection at 220 nM. Retention times: trans vinyl sulfone, 16.0 min; cis vinyl sulfone, 17.1 min; product (syn), 7.6 min; product (anti), 8.0 min.

The mixture was warmed to room temperature, and the organic layer was concentrated to a volume of approximately 9.8 L while maintaining a temperature of <30° C. The residue was dissolved in ethyl acetate (74 L), washed with 15% wt NaCl solution (2×19.6 L) and concentrated to a volume of approximately 9.8 L. The mixture was azeotropically distilled with MTBE (2×49 L) to a final volume of 9.8 L with <10% ethyl acetate relative to MTBE. The concentration of product in solution was adjusted to 40–45% by weight by the removal or addition of MTBE, heptane (14.7 L) was slowly added, and the resulting slurry was stirred for at least 4 hours until the concentration of product in the mother liquor was <30 mg/mL. The precipitate was filtered, washed with cold MTBE/heptane (1:3 v/v, 9.8 L), and dried under vacuum (100 mm Hg with nitrogen sweep) at 30° C. to provide 4.82 kg (63.6%) of the desired product with 0.74% of the anti diastereomer.

$^1$H NMR (300 MHz, $CDCl_3$) δ 7.9 (d, 2H), 7.3 (d, 2H), 7.1 (br d, 4H), 4.35 (m, 1H), 4.05 (dd, 1H), 3.8 (dd, 1H), 3.6 (m, 1H), 3.45 (m, 1H), 3.1 (dd, 1H), 1.4 (s, 3H), 1.35 (s, 3H).

EXAMPLE 4F (1S)-1-((4S)-2,2-dimethyl-1,3-dioxolan-4-yl)-2-((4-(4'-(trifluoromethoxy)phenoxy)phenyl)sulfonyl)ethyl (hydroxy)formamide A 100 L flask equipped with an overhead stirrer, a nitrogen inlet, a reflux condenser, and a thermocouple was charged with Example 4E (3.5 kg), sodium formate (0.350 kg), isopropyl acetate (30.45 kg), 2,2,2-trifluoroethyl formate (9.50 kg), and formic acid (1.05 kg). The mixture was heated to an internal temperature 60° C. and maintained at this temperature with continuous stirring until HPLC showed less than 0.5% starting material (about 5 hours). HPLC conditions: Luna C-8 Phenomenex column at 20° C., mobile phase was a gradient of 55% $KH_2PO_4$ buffer (pt 1 2.3)/ 45% acetonitrile to 33/67 over 55 min at a flow rate of 1 mL/min; UV detection at 210 nM. Retention times: starting material, 41.4, product, 32.3 min.

The reaction was cooled to <30° C. and treated with 5% wt sodium chloride solution (17.68 kg). The organic phase was washed with 5% wt sodium bicarbonate solution (17.79 kg portions) until the pH of aqueous layer was ≧8.0, washed with 5% wt sodium chloride solution (17.68 kg) (aqueous phase pH 7.0), stored at ambient temperature for two days, and then combined with product obtained from a second formylation reaction (3.27 kg) to provide approximately 6.60 kg of combined product. The solutions were combined and distilled under vacuum. Residual 2,2,2-trifluoroethanol was removed by azeotropic distillation with isopropyl acetate and monitored by gas chromatography until the ratio of isopropyl acetate to 2,2,2-trifluoroethanol was 1000:1. GC-FID conditions: Stabilwax-DB column (Restek Corp. cat#10823, lot#15531A, L=30 m, ID=0.25 mm), heater at 250° C., oven temperature gradient: 40° C. from 0 to 4 min then 10 ° C./min to 100° C., then held at 100° C. 10 min, post-run 5 min; 1 μL injection volume. Retention times: isopropyl acetate, 4.5 min, 2,2,2-trifluoroethanol, 9.5 min.

The concentration of the solution was adjusted by solvent removal under vacuum to 25% wt product in isopropyl acetate. The solution was treated with heptanes (20 L) and stirred for 15 hours, at which time the concentration of product in the mother liquor was measured by HPLC at 11 mg/mL. The product was collected by filtration, rinsed with a solution of 1:1 (v/v) isopropyl acetate/heptanes (10 L), and dried under vacuum (100 mm Hg with a nitrogen sweep at 55° C.) to provide 5.89 kg (89% yield) of the desired product with a chiral purity of 99.8% ee. Chiral HPLC conditions: Daicel Chiral PAK AD 4.6×250 mm column at ambient temperature 0.3% v/v trifluoroacetic acid in ethanol (200 proof) over 30 minutes with a flow rate of 0.3 mL/min, UV detection at 243 nM. Retention times: desired product, ~17 min; enantiomer, ~14 min.

$^1$H NMR (300 MHz, $CDCl_3$) δ 8.40 (s, 1H), 7.85–7.90 (m, 0.5H), 7.80–7.90 (m, 2H), 7.20–7.35 (m, 2H), 7.05–7.15 (m, 4H), 4.75–4.85 (m, 0.5H), 4.20–4.35 (m, 2H), 4.0–4.15 (m, 1H), 3.75–3.90 (m, 2H), 3.35 (dd, 0.5 H), 3.10 (dd, 0.5H), 1.42 (s, 3H), 1.30 (s, 3H); two rotomers of the formamide are observed for some signals.

What is claimed is:

1. A process for the conversion of an N-hydroxylamine to an N-hydroxyformamide comprising reacting the N-hydroxylamine with 2,2,2-trifluoroethylformate in an optionally buffered solvent.

2. A process according to claim 1, wherein the N-hydroxylamine is selected from the group consisting of N-benzyl-N-hydroxylamine, ((1S)-1-(N-hydroxyamino)

ethyl)benzene, 3-((2S)-2-(N-hydroxyamino)-3-((4'-(trifluoromethoxy)(1,1'-biphenyl)-4-yl)oxy)propyl)-5,5'-dimethyl-2,4-dimethyl-2,4-imidazolidinedione, and (4S)-4-((1S)-1-(Hydroxyamino)-2-((4-(4'-(trifluoromethoxy)phenoxy)phenyl)sulfonyl)ethyl)-2,2-dimethyl-1,3-dioxolane.

3. A process according to claim 2 wherein the N-hydroxylamine is 3-((2S)-2-(N-hydroxyamino)-3-((4'-(trifluoromethoxy)(1,1'-biphenyl)-4-yl)oxy)propyl)-5,5'-dimethyl-2,4-dimethyl-2,4-imidazolidinedione.

4. A process according to claim 2 wherein the N-hydroxylamine is (4S)-4-((1S)-1-(hydroxyamino)-2-((4-(4'-(trifluoromethoxy)phenoxy)phenyl)sulfonyl)ethyl)-2,2-dimethyl-1,3-dioxolane.

5. A process according to claim 1 wherein the buffer is selected from the group consisting of a carbonate salt, a bicarbonate salt, a phosphate salt, a tertiary amine, an optionally substituted pyridine, imidazole, and a carboxylate salt.

6. A process according to claim 5 wherein the buffer is selected from the group consisting of imidazole and a carboxylate salt.

7. A process according to claim 6 wherein the buffer is selected from the group consisting of imidazole and sodium formate.

8. A process according to claim 1, wherein the solvent is selected from the group consisting of tetrahydrofuran, methyl tert-butyl ether, ethyl acetate, isopropyl acetate, 2,2,2-trifluoroethanol, formic acid, toluene, and mixtures thereof.

9. A process according to claim 8 wherein the solvent is selected from the group consisting of tetrahydrofuran, isopropyl acetate, methyl tert-butyl ether, formic acid, and mixtures thereof.

10. A process according to claim 1 which is conducted at about 50° C. to about 70° C.

11. A process according to claim 1 which is conducted for about to about 24 hours.

* * * * *

UNITED STATES PATENT AND TRADEMARK OFFICE
CERTIFICATE OF CORRECTION

PATENT NO. : 6,350,902 B2  Page 1 of 1
DATED : February 26, 2002
INVENTOR(S) : David R. Hill et al.

It is certified that error appears in the above-identified patent and that said Letters Patent is hereby corrected as shown below:

<u>Column 10,</u>
Line 18, replace "about to about 24 hours" with -- about 3 to about 24 hours --

Signed and Sealed this

Twenty-second Day of October, 2002

Attest:

Attesting Officer

JAMES E. ROGAN
*Director of the United States Patent and Trademark Office*